United States Patent [19]

zur Hausen et al.

[11] Patent Number: 4,780,547

[45] Date of Patent: Oct. 25, 1988

[54] PROCESS FOR THE PRODUCTION OF $C_1$– TO $C_6$-N-ALKYLPYRROLIDONES FROM SUCCINIC ANHYDRIDE AND/OR $C_1$– TO $C_6$-N-ALKYLSUCCINIMIDES

[75] Inventors: Manfred zur Hausen, Marl; Werner Otte, Dorsten, both of Fed. Rep. of Germany

[73] Assignee: Huels Aktiengesellschaft, Marl, Fed. Rep. of Germany

[21] Appl. No.: 69,739

[22] Filed: Jul. 6, 1987

[30] Foreign Application Priority Data

Jul. 7, 1986 [DE] Fed. Rep. of Germany ....... 3622759

[51] Int. Cl.$^4$ ........................................... C07D 207/10
[52] U.S. Cl. .................................... 548/552; 548/554
[58] Field of Search ................................ 548/552, 554

[56] References Cited

U.S. PATENT DOCUMENTS

| | | | |
|---|---|---|---|
| 3,109,005 | 10/1963 | Lidov | 548/554 |
| 3,448,118 | 6/1969 | Chichery et al. | 548/554 X |
| 3,634,346 | 1/1972 | McKeon et al. | 548/552 X |
| 3,745,164 | 7/1973 | Adamek | 548/552 X |
| 3,812,148 | 5/1974 | Hollstein et al. | 548/554 |
| 3,812,149 | 5/1974 | Hollstein | 548/554 |
| 3,884,936 | 5/1975 | Hollstein | 548/554 |

FOREIGN PATENT DOCUMENTS

| | | | |
|---|---|---|---|
| 201632 | 4/1955 | Australia | 548/552 |
| 830194 | 1/1952 | Fed. Rep. of Germany . | |
| 1620191 | 3/1974 | Fed. Rep. of Germany . | |
| 1192670 | 5/1970 | United Kingdom . | |
| 1358862 | 7/1974 | United Kingdom . | |
| 259889 | of 0000 | U.S.S.R. . | |

OTHER PUBLICATIONS

Romanovski, V. I., Sokolova, A. I., and N. I. Tat'yanchikova, "Synthesis of N–Methyl–-Pyrrolidone from Succinic Acid", Chemical Abstracts, vol. 60, 1680a.

Beilsteins Handbuck der Organischen Chemie, EIII/IV 21, 3145 (1978).

Encyclopedia of Chemical Technology, 3rd Ed., vol. 19, (1982) Kirk-Othmer, pp. 514–518.

Primary Examiner—Joseph Paul Brust
Attorney, Agent, or Firm—Millen & White

[57] ABSTRACT

$C_1$– to $C_6$-N-alkylpyrrolidones are produced from succinic anhydride and $C_1$– to $C_6$-N-alkylamines or $C_1$– to $C_6$—N-alkylsuccinimides. They are hydrogenated in the presence of a Ni hydrogenation catalyst containing from about 0.1–3% of one or several alkaline earth oxides and/or iron oxide and/or chromium oxide, at temperatures of from about 180°–250° C. and under pressures of at least about 100 bar. Preferably, a Ni catalyst is utilized which contains a total of 1.5–2% alkaline earth oxides, iron oxide and chromium oxide.

16 Claims, No Drawings

PROCESS FOR THE PRODUCTION OF $C_1$— TO $C_6$-N-ALKYLPYRROLIDONES FROM SUCCINIC ANHYDRIDE AND/OR $C_1$— TO $C_6$-N-ALKYLSUCCINIMIDES

BACKGROUND OF THE INVENTION

This invention relates to a process for the production of $C_1$— to $C_6$—N-alkylpyrrolidones from succinic anhydride and $C_1$— to $C_6$-alkylamines and/or, $C_1$— to $C_6$—N-alkylsuccinimide.

N-alkylpyrrolidones are of importance as solvents and intermediates and can undergo a number of characteristic chemical reactions (Kirk-Othmer, Vol. 19 (1982), p. 514–520, GB-Pat. No. 1 192 670, GB-Pat. No. 1 358 862 and U.S. Pat. No. 3,634,346).

By following conventional methods, N-alkylpyrrolidones have been obtained from the corresponding N-alkylsuccinimides by electrochemical reduction (Beilstein E III/IV 21: 3245), from pyrrolidin-2-one and methanol on $Al_2O_3$ (German Pat. No. 830,194), from dihydrofuran-2-one and methylamine (Beilstein E III-/IV 21: 3145), from succinic acid by way of N-methylsuccinimide in the presence of Ra-Ni and dioxane at 200°–215° C. and 200–220 bar (Khim. Prom. 1963 (7): 491–492), or from succinimide in the presence of the alcohol corresponding to the desired alkyl group, on cobalt or nickel catalysts at 200°–280° C. and under a pressure of 200–300 bar (Russian Pat. No. 259,889), as well as the method according to DAS No. 1,620,191=U.S. Pat. No. 3,448,118=GB-Pat. No. 1 089 834 wherein succinic acid is reacted with alkylamine and hydrogen in the presence of Raney metals, Co, Ni, Ru or Pd catalysts at 200°–300° C. and under pressures of 50 bar. Contrary to the statements in the specification (column 3, line 3), the examples reveal that the process evidently cannot be performed without the use of a solvent or diluent (water or dioxane).

In the above-mentioned methods, yields of alkylpyrrolidone of at best 80% are obtained.

Starting with N-methylsuccinimide (Khim. Prom. 491-2, 1963), a yield of merely 71.6% is achieved on Raney Ni.

SUMMARY OF THE INVENTION

It is an object of this invention to provide a process which employs the readily available raw materials of succinic anhydride as well as $C_1$— to $C_6$—N-alkylamines or $C_1$— to $C_6$—N-alkylsuccinimide in the production of the corresponding $C_1$— to $C_6$—N-alkylpyrrolidones in economical fashion and good yields.

Upon further study of the specification and appended claims, further objects and advantages of this invention will become apparent to those skilled in the art.

These objects have been achieved by providing a process for the production of a $C_1$— to $C_6$—N-alkylpyrrolidone from a) succinic anhydride and a $C_1$— to $C_6$—alkylamine and/or b) a $C_1$— to $C_6$—N-alkylsuccinimide in the presence of a catalytically effective amount of a Ni hydrogenation catalyst containing from about 0.1–3% of one or several alkaline earth metal oxides and/or iron oxide and/or chromium oxide, at a temperature of from about 180°–250° C. and under a pressure of at least about 100 bar.

DETAILED DISCUSSION

It has been found surprisingly that the process of this invention results in $C_1$— to $C_6$—N-alkylpyrrolidones in yields of about 85% by using Ni catalysts containing as the activators and/or stabilizers small amounts, e.g., a total of about 0.1–3% of alkaline earth metal oxides (e.g., of Mg, Ca) and/or iron oxide and/or chromium oxide. One or several alkaline earth metal oxides can be utilized. The preferred iron oxide is $Fe_2O_3$; the preferred chromium oxide is $Cr_2O_3$ or $Cr_3O_4$. Preferably, the activators are employed in total amounts of from about 1.5 to about 2%.

Especially advantageous results are obtained by using the alkaline earth metal oxides in combination with iron oxide and chromium oxide, preferably with $Fe_2O_3$ and $Cr_2O_3$ or $Cr_3O_4$, preferably in total amounts of 1.5–2%. Typical amounts of each oxide when employed are alkaline earth metal oxides: 0–2 wt%; Fe: 0–1 wt%, Cr: 0–1 wt%.

The preparation of the catalysts of this invention is fully conventional in all respects, as described in R. L. Augustine: "Catalytic Hydrogenation" and Alvin B. Stiles: "Catalyst Manufacture", Marchl. Dekke inc. New York, 1983.

The process of this invention is carried out at temperatures of 180°–250° C., preferably in a temperature range from 200° to 230° C.

The process of this invention should be conducted under a hydrogen pressure range above 100 bar, preferably above 200 bar. The preferred operating pressure range is from about 250 to about 320 bar. A Typical LHSV (Liquid Hourly Space Velocity)-range is from about 0.2 to about 0.5. In the sump-phase the reaction times for hydrogenation are 4–8 hours.

The process of this invention can be performed discontinuously as well as continuously, for example in an agitated autoclave or a tubular reactor. The installations required for hydrogenation are fully conventional and are well known to those skilled in the art. It is also possible to perform the process of this invention in either the bottoms phase or trickling phase.

In discontinuous operation, the process is usually conducted in the bottoms phase in an autoclave in the presence of a pulverulent catalyst. The particle sizes for the pulverent catalyst range for example form about 3 $\mu$m to about 15 $\mu$m. Suitable ranges for the molar ratio of succinic anhydride to methylamine are from about 1:1 to about 1:2. the preferred ranges from about 1:1 to about 1:1.2.

Suitable base nickel catalyst are all those previously known for the underlying reaction and related reactions. These include
Suitable base Ni catalysts are disclosed in R. L. Augustine: "Catalytic Hydrogenation". Suitable base Ni catalysts are for example: Harshaw Ni 5124, Ni 3266, Ni 1404.

The modified catalysts are known per se as discussed above or can be prepared by conventionally modifying known Ni catalysts. See, e.g., Alvin B. Stiles: "Catalyst Manufacture" Marchl. Dekke inc. New York, 1983.

The amount of total catalyst used is typically 1–5 wt% based on the amount of succinic compounds for the discontinous process and about 0.1% for the continous process in the trickling phase.

The continuous mode of operation is especially advantageous in the process of this invention. The starting materials are customarily passed in the liquid form over the catalyst arranged in pieces within the tubular reactor, for example following the trickling phase principle, while the hydrogen is conducted in cocurrent or countercurrent mode through the tubular reactor. It is advantageous to recirculate the excess hydrogen. Yields of greater than 80%, preferably greater than 85% and selectivities of at least 90%, preferably greater than 92% can be achieved by the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

A 400 ml flow reactor is charged with a Ni catalyst (NiO: 80%; CaO: 0.5%; MgO: 0.6%; $Fe_2O_3$: 0.2%; $Cr_3O_4$: 0.5%; $SiO_2$: 9%; $Al_2O_3$: 7%) and fed per hour with 80 ml of N-methylsuccinimide. Hydrogenation takes place under a total pressure of 300 bar and at 200° C. The results are listed in the table.

EXAMPLE 2

The process is performed as in Example 1, but the temperature is increased to 250° C. The results are set forth in the table.

Comparable results are obtained by using, in place of N-methylsuccinimide, succinic anhydride and methylamine in a molar ratio of 1:1.1.

EXAMPLE 3

The process is conducted as in Example 1, but using a catalyst with 82% NiO, 1.2% CaO, 0.3% MgO, 0.1% $Fe_2O_3$, 8.5% $SiO_2$ and 3% $Al_2O_3$. The results are indicated in the table. Comparable results are obtained by using, in place of N-methylsuccinimide, N-ethyl and, respectively, N-propylsuccinimide.

EXAMPLE 4

The process is carried out as in Example 1, but with the use of a catalyst with 79% NiO, 0.8% CaO, 0.7% MgO, 10% $SiO_2$ and 6.5% $Al_2O_3$. The thus-obtained results are set out in the table.

EXAMPLE 5

The process is performed as in Example 1, but utilizing a catalyst with 81% NiO, 0.7% CaO, 0.5% MgO, 0.5% $Cr_2O_3$, 8% $SiO_2$ and 5% $Al_2O_3$. The thus-achieved results are listed in the table.

EXAMPLE 6

The process is conducted as in Example 1, but with the use of a catalyst with 80% NiO, 0.3% $Fe_2O_3$, 10% $SiO_2$ and 7% $Al_2O_3$. The resultant data are set forth in the table.

EXAMPLE 7

The process is carried out as in Example 1, but employing a catalyst with 81% NiO, 0.4% $Fe_2O_3$, 0.6% $Cr_2O_3$, 9% $SiO_2$ and 6% $Al_2O_3$. The thus-obtained results are complied in the table.

EXAMPLE 8

The process is conducted as in Example 1, but using a catalyst with 82% NiO, 0.7% $Cr_2O_3$, 9% $SiO_2$ and 6% $Al_2O_3$. The results obtained are compiled in the table.

The percentage points missing from 100% in the catalyst compositions refer to organic binders (for example graphite).

COMPARATIVE EXAMPLE 1

The process is performed as in Example 1, but using, instead of the Ni catalyst of this invention, a catalyst containing 78% NiO (support: 12% $Al_2O_3$, 17% $SiO_2$ and 3% graphite). The results can be seen from the table.

COMPARATIVE EXAMPLE 2

The process is conducted as in Example 1, but pressure is lowered to 100 bar. The results can be derived from the table.

|  | Compilation of Test Results | | | | | | | |
|---|---|---|---|---|---|---|---|---|
|  | NMPIN[1] % | gamma-BL[2] % | NMP[3] % | NMSI[4] % | HBSA[5] % | BNMSA[6] % | Remainder % | Yield mol-% |
| Example | | | | | | | | |
| 1 | 1.6 | 0.8 | 84.8 | 2.8 | 3.0 | 2.9 | 4.1 | 87.9 |
| 2 | 3.3 | 0.3 | 81.4 | 2.0 | 3.0 | 5.1 | 4.9 | 85.2 |
| 3 | 1.2 | 1.1 | 83.1 | 3.1 | 3.2 | 3.4 | 4.9 | 86.9 |
| 4 | 1.3 | 0.9 | 82.5 | 3.2 | 3.0 | 4.2 | 4.9 | 86.5 |
| 5 | 2.1 | 0.6 | 83.6 | 2.9 | 3.1 | 3.2 | 4.5 | 87.0 |
| 6 | 1.4 | 0.5 | 82.1 | 3.5 | 2.9 | 3.8 | 5.8 | 86.4 |
| 7 | 2.2 | 1.0 | 82.4 | 3.0 | 2.8 | 3.5 | 5.1 | 86.0 |
| 8 | 1.8 | 0.8 | 82.7 | 3.2 | 3.0 | 4.1 | 4.4 | 86.3 |
| Comparative Example | | | | | | | | |
| 1 | 0.7 | 2.1 | 70.0 | 17.1 | 5.2 | 3.4 | 1.5 | 73.3 |
| 2 | 2.1 | 1.1 | 58.4 | 27.6 | 2.8 | 3.1 | 4.9 | 62.8 |

[1] = N—Methylpyrrolidine
[2] = gamma-Butyrolactone
[3] = N—Methylpyrrolidone
[4] = N—Methylsuccinimide
[5] = Hydroxybutyric acid N—methyl amide
[6] = bis-N—Methylsuccinamide The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a $C_1$— to $C_6$—N-alkylpyrrolidone comprising hydrogenating a) succinic anhydride and a $C_1$— to $C_6$—N-alkylamine and/or b) a $C_1$— to $C_6$—N-alkylsuccinimide in the presence of a catalytically effective amount of a Ni hydrogenation catalyst containing a total amount of from about 0.1–3% of an alkaline earth metal oxide, iron oxide, chromium oxide or a mixture thereof, at a temperature of from about 180° to about 250° C. and under a hydrogen pressure of above 100 bar.

2. A process of claim 1, wherein said hydrogenation is carried out at a temperature of from about 200° to about 230° C.

3. A process according to claim 1, wherein said hydrogenation is conducted under a hydrogen pressure of at least 200 bar.

4. A process of claim 1, wherein said hydrogenation is conducted under a pressure range of from about 250 to about 320 bar.

5. A process of claim 1, wherein said alkaline earth metal oxide is MgO.

6. A process of claim 1, wherein said alkaline earth metal oxide is CaO.

7. A process of claim 1, wherein said chromium oxide is $Cr_2O_3$.

8. A process of claim 1, wherein said chromium oxide is $Cr_3O_4$.

9. A process of claim 1, wherein said iron oxide is $Fe_2O_3$.

10. A process of claim 1, wherein said Ni catalyst contains from about 1.5 to about 2% alkaline earth metal oxides and/or iron oxide and/or chromium oxide.

11. A process of claim 10, wherein said alkaline earth metal oxide is MgO.

12. A process of claim 10, wherein said alkaline earth metal oxide is CaO.

13. A process of claim 1, wherein said Ni catalyst contains an alkaline earth metal oxide, an iron oxide and a chromium oxide.

14. A process of claim 13, wherein said alkaline earth metal oxide is MgO, CaO or a mixture thereof, said iron oxide is $Fe_2O_3$ and said chromium oxide is $Cr_2O_3$, $Cr_3O_4$ or a mixture thereof.

15. A process of claim 10, wherein said Ni catalyst contains an alkaline earth metal oxide, an iron oxide and a chromium oxide.

16. A process of claim 15, wherein said alkaline earth metal oxide is selected from MgO, CaO, or mixtures thereof, said iron oxide is $Fe_2O_3$ and said chromium oxide is selected from $Cr_2O_3$, $Cr_3O_4$ or mixtures thereof.

* * * * *